United States Patent [19]
Arpe et al.

[11] Patent Number: 4,650,915
[45] Date of Patent: Mar. 17, 1987

[54] PROCESS FOR PREPARING P-CHLOROTOLUENE AND/OR M-CHLOROTOLUENE

[75] Inventors: Hans-Jürgen Arpe, Frankfurt am Main; Heinz Litterer, Wiesbaden; Norbert Mayer, Frankfurt am Main, all of Fed. Rep. of Germany

[73] Assignee: Hoechst Aktiengesellschaft, Frankfurt, Fed. Rep. of Germany

[21] Appl. No.: 764,511

[22] Filed: Aug. 9, 1985

Related U.S. Application Data

[63] Continuation of Ser. No. 600,598, Apr. 17, 1984, abandoned, which is a continuation of Ser. No. 406,472, Aug. 9, 1982, abandoned.

[30] Foreign Application Priority Data

Aug. 11, 1981 [DE] Fed. Rep. of Germany ....... 3131682

[51] Int. Cl.$^4$ ............................................. C07C 17/38
[52] U.S. Cl. .................................. 570/202; 570/207; 570/211
[58] Field of Search .................. 570/202, 207, 211

[56] References Cited

U.S. PATENT DOCUMENTS

| 2,958,708 | 11/1960 | Fleck et al. | 570/211 |
| 3,742,073 | 6/1973 | Bacha et al. | 570/202 |
| 4,061,724 | 12/1977 | Grose et al. | 423/339 |
| 4,254,062 | 3/1981 | Wambach et al. | 570/211 |
| 4,368,339 | 1/1983 | Tada et al. | 570/202 |

FOREIGN PATENT DOCUMENTS

| 625404 | 8/1961 | Canada | 570/211 |
| 46068 | 2/1982 | European Pat. Off. | 570/211 |
| 46665 | 3/1982 | European Pat. Off. | 570/202 |
| 62261 | 10/1982 | European Pat. Off. | 570/202 |
| 1543020 | 4/1972 | Fed. Rep. of Germany . | |
| 31627 | 2/1982 | Japan | 570/211 |
| 902724 | 8/1962 | United Kingdom . | |
| 1212809 | 12/1968 | United Kingdom . | |

Primary Examiner—Natalie Trousof
Assistant Examiner—Joseph A. Boska
Attorney, Agent, or Firm—Curtis, Morris & Safford

[57] ABSTRACT

The invention relates to a process for preparing p-chlorotoluene and/or m-chlorotoluene by ring-chlorination of toluene by using the following two pages (a) and (b) when further processing the toluene chlorination product composed of mixed isomers:

(a) Isolation of p-chlorotoluene from a mixture of o-, m- and p-chlorotoluene by selective adsorption of p-chlorotoluene onto a mesoporous or macroporous zeolite and subsequent desorption of p-chlorotoluene (b) Treatment of an o-chlorotoluene-rich mixture of isomers with an isomerization catalyst.

For the exclusive preparation of p-chlorotoluene first p-chlorotoluene is isolated and removed from the toluene chlorination product in stage (a). The remaining mixed isomers are then treated in stage (b) to increase their content of m- and p-isomers and then returned into stage (a).

For the preparation of m-chlorotoluene and, if appropriate, additionally of p-chlorotoluene first the toluene chlorination product is treated in stage (b) to increase its content of m- and, if appropriate, p-isomer. p-Chlorotoluene is then isolated in stage (a) and returned to stage (b), or, if appropriate, removed. The remaining mixture essentially comprising o- and m-isomers is separated by distillation or adsorption and o-chlorotoluene is then returned into stage (b) and m-chlorotoluene is removed.

3 Claims, No Drawings

PROCESS FOR PREPARING P-CHLOROTOLUENE AND/OR M-CHLOROTOLUENE

This application is a continuation of application Ser. No. 600,598, filed 04/17/84 which was a continuation of application Ser. No. 406,472 filed 08/09/82, each now abandoned.

The chlorination of toluene in the presence of catalysts is known to produce the ring-chlorinated isomeric o-, m- and p-monochlorotoluenes in a ratio which varies according to the type of catalyst used and the reaction conditions chosen. Thus, for example, the chlorination of toluene at 50° C. in the presence of $FeCl_3$ as catalyst up to a density of 1.043 g/cm$^3$ (20° C.) leads to a product comprising 19% by weight of toluene, 49% by weight of o-chlorotoluene, 2% by weight of m-chlorotoluene and 25.5% by weight of p-chlorotoluene. Apart from these, 4.5% of dichlorotoluene are additionally formed (Ullmanns Encyl. der techn. Chemie [Ullmann's Encyclopedia of Industrial Chemistry] (1975), Volume 9, page 512). The use of $TiCl_4$, $SnCl_4$, $WCl_6$ or $ZrCl_4$ as catalysts at a chlorination temperature of 10°–30° C. increases the o-chlorotoluene content to 75% by weight (U.S. Pat. No. 3,000,975), while the use of disulfide dichloride and the metal chlorides mentioned or of sulfur and $SbCl_3$ shifts the isomeric ratio in favor of p-chlorotoluene (U.S. Pat. No. 1,946,040). There is no successful instance of obtaining a single isomer by a suitable choice of catalyst or reaction conditions. All these processes therefore require a subsequent separation of the reaction mixture into the pure isomers, which separation is customarily carried out in two stages where, in a first working-up stage, which is expensive in outlay and energy, o-chlorotoluene (boiling point 158.5° C.) is separated as top product by distillation, for example in a bubble cap column having over 200 theoretical plates, from a bottom comprising m- and p-chlorotoluene. Due to the small difference in the boiling points of these isomers (161.2° C. and 161.5° C. respectively), it is no longer possible to separate their mixture by distillation. Pure p-chlorotoluene (melting point 7.6° C.) must therefore be separated in a second step by crystallization from the m-isomer, which has a lower melting point (melting point −48.7° C.).

The object of the invention was to simplify this involved separation procedure. Another object of the invention was to increase the yield of industrially important p-chlorotoluene and also—in the case of demand—to enable a simple preparation and isolation of m-chlorotoluene.

The process according to the invention for preparing m-chlorotoluene comprises a plurality of cycles with the steps of:
- (a) chlorinating toluene to form a toluene chlorination product rich in o-chlorotoluene;
- (b) after the first cycle, forming a mixture consisting of a first and second recycled component and the toluene chlorination product;
- (c) treating the mixture, or in the first cycle the toluene chlorination product, with an isomerization catalyst comprising a zeolite of the pentasil, mordenite or faujasite type to form an isomerization product with increased content of m-chlorotoluene;
- (d) isolating p-chlorotoluene from the isomerization product by selective adsorption of p-chlorotoluene onto a mesoporous or macroporous zeolite and subsequent desorption of p-chlorotoluene to form the first recycled component and to leave an unadsorbed phase lean in p-chlorotoluene and rich in o- and m-chlorotoluene;
- (e) separating the unadsorbed phase by distillation or adsorption; and
- (f) removing the m-chlorotoluene to leave o-chlorotoluene as the second recycled component.

The process may be operated in a continuous manner in which fresh purified toluene chlorination product is added in each cycle, as described above, or the process may be operated in a discontinuous manner in which no further toluene chlorination product is added after the first cycle.

The process according to the invention for preparing p-chlorotoluene comprises a plurality of cycles with the steps of:
- (a) chlorinating toluene to form a toluene chlorination product rich in o-chlorotoluene;
- (b) after the first cycle, forming a mixture consisting of a recycled component and the toluene chlorination product;
- (c) isolating p-chlorotoluene from the mixture, or in the first cycle from the toluene chlorination product, by selective adsorption of p-chlorotoluene onto a mesoporous or macroporous zeolite and subsequent desorption of p-chlorotoluene to leave an unadsorbed phase lean in p-chlorotoluene and rich in o-chlorotoluene; and
- (d) treating the unadsorbed phase with an isomerization catalyst comprising a zeolite of the pentasil, mordenite or faujasite type to form the recycled component with increased content of m- and p-chlorotoluene.

The process may be operated in a continuous manner in which fresh purified toluene chlorination product is added in each cycle, as described above, or the process may be operated in a discontinuous manner in which no further toluene chlorination product is added after the first cycle.

The process according to the invention for preparing both p-chlorotoluene and m-chlorotoluene comprises a plurality of cycles with the steps of:
- (a) chlorinating toluene to form a toluene chlorination product rich in o-chlorotoluene;
- (b) after the first cycle, forming a mixture consisting of a recycled component and the toluene chlorination product;
- (c) treating the mixture, or in the first cycle the toluene chlorination product, with an isomerization catalyst comprising a zeolite of the pentasil, mordenite or faujasite type to form an isomerization product with increased content of p- and m-chlorotoluene;
- (d) isolating p-chlorotoluene from the isomerization product by selective adsorption of p-chlorotoluene onto a mesoporous or macroporous zeolite and subsequent desorption and removal of p-chlorotoluene to leave an unadsorbed phase lean in p-chlorotoluene and rich in o- and m-chlorotoluene;
- (e) separating the unadsorbed phase by distillation or adsorption; and
- (f) removing the m-chlorotoluene to leave o-chlorotoluene as the recycled component.

The process may be operated in a continuous manner in which fresh purified toluene chlorination product is added in each cycle, as described above, or the process may be operated in a discontinuous manner in which no further toluene chlorination product is added after the first cycle.

Examples of suitable mesoporous or macroporous zeolites (pore diameter >0.46 nm) for the selective adsorption of p-chlorotoluene from the mixture of isomers are modified pentasils and modified X and Y zeolites. A suitable modification is obtained by ion exchange and/or impregnation using monovalent or polyvalent cations. Possible cations are $H^+$, $NH_4^+$, $Na^+$, $K^+$, $Ca^{2+}$, $Sr^{2+}$, $Ba^{2+}$, $Zr^{4+}$ or $Co^{2+}$. Y-Zeolites exchanged using $K^+$, $Ba^{2+}$ or $K^+/Ba^{2+}$ are particularly suitable. Additional incorporation of protons (via the $NH_4^+$ form) produces maximum p-chlorotoluene selectivity at maximum dynamic adsorption capacity for highly exchanged potassium or barium zeolites of the Y type.

Another modification possibility, to improve the p-chlorotoluene selectivity of pentasils, is a controlled precoking step, which can be carried out instead of ion exchange or impregnation or in addition to these measures. This step involves bringing hydrocarbons, preferably aromatic hydrocarbons such as toluene, for a brief period into contact with the pentasil at temperatures of 500° to 800° C.

To bring the zeolites into a usable form generally requires binder materials, for example the oxides, hydroxides or hydroxychlorides of aluminum or the oxides or hydroxides of silicon.

The adsorption is carried out at temperatures of 150° to 300° C., preferably at 180° to 280° C., and under a pressure of 1 to 50 bar, preferably 5 to 25 bar. The subsequent desorption is generally carried out with the aid of a hydrocarbon or with the aid of steam, ammonia, nitrogen, hydrogen or another inert gas, preferably at an elevated temperature and under a reduced pressure (relative to the adsorption).

The isomerization can be effected, for example, by the action of Friedel-Crafts catalysts, say $AlCl_3$ or HCl, at temperatures of about 100° C. (J. Am. Chem. Soc. 61 (1939), 2128; J. Org. Chem. 27, (1962), 3464–9). Other suitable Friedel-Crafts catalysts are $BF_3$, $BF_3.HF$, $H_3PO_4$, $SnCl_4$, $FeCl_3$, $SbCl_5$, $TiCl_4$ and $ZnCl_2$, if appropriate in combination with protonic acids.

However, preferable catalysts for the isomerization of the chlorotoluene are synthetic zeolites of the pentasil type, such as ZSM-5, ZSM-8 or ZSM-11—which are accessible, for example, according to British Pat. No. 1,567,948—and natural or synthetic zeolites of the mordenite or faujasite type. The Si/Al ratio of the pentasils is preferably about 25 to 2,000, and the ratio of the mordenites is preferably 5 to 100. In the case of pentasils or mordenites having a higher aluminum content, treatment with mineral acids, organic acids or chelating substances can obtain partial removal of skeletal aluminum, the result being an increase in activity. For use in industry, the zeolites mentioned are brought, with the aid of binders, into the extruded form, the choice of binder influencing the selectivity and operating life.

Suitable binder materials are above all the oxides, hydroxides or hydroxychlorides of aluminum and the oxides or hydroxides of silicon as well as clays and clay materials. The zeolites are converted by ion exchange into their catalytically active forms. Particularly suitable cations are $H^+$, $NH_4^+$, $Mg^{2+}$, $Ca^{2+}$, rare earth metal ions and combinations of these elements.

The zeolite catalysts are additionally activated, in the customary manner, by calcination. In some cases it is advantageous to repeat ion exchange and calcination several times. The calcination is preferably carried out at 350° to 700° C. To obtain better stabilization, it is sometimes advantageous to carry out the calcination in the presence of steam, ammonia or their mixtures at temperatures between 600° and 900° C.

The isomerization can be carried out not only in the gas phase but also in the liquid phase. Suitable process conditions for the liquid phase isomerization are temperatures of 200° to 350° C., preferably 200° to 300° C., and pressures of 5 to 100 bar, preferably 5 to 60 bar. To reduce the rate of coke deposition, hydrogen is preferably added in liquid phase isomerization. Transalkylation of chlorotoluenes, which commences at temperatures above 300° C., can be suppressed by dilution with aromatic hydrocarbons, such as toluene. The weight hourly space velocity (WHSV) should preferably be between 0.5 and 10 $h^{-1}$.

The isomerization in the gas phase is generally carried out at temperatures of 330° to 550° C., preferably at 330° to 440° C., and under pressures of 1 to 60 bar, preferably 5 to 40 bar. In contrast to the liquid phase, the gas phase reaction absolutely requires the feeding of hydrogen into the reaction mixture to avoid too rapid deactivation of the catalysts. The molar ratio of hydrogen to chlorotoluene should be between 1:1 and 12:1. The WHSV of the catalyst should in general be 1 $h^{-1}$ to 10 $h^{-1}$. Spent catalysts are generally regenerated by controlled burning off using oxygen-containing gases.

If it is intended to prepare only p-chlorotoluene, toluene is ring-chlorinated preferably in the presence of $FeCl_3$ and $S_2Cl_2$ at 15°–75° C. under atmospheric pressure and at a molar ratio of chlorine to toluene of 0.8 to 1.0. After neutralization, for example by means of milk of lime, toluene and higher chlorinated by-products are separated off by distillation, and a "purified toluene chlorination product", which in this case is comprised of somewhat above 50% by weight of o-chlorotoluene and about 0.3 to 1.5% by weight of m-chlorotoluene, the remainder being p-chlorotoluene, is obtained.

When operating in a discontinuous manner, p-chlorotoluene is separated from this mixture of isomers and subsequently isolated, by desorption, in a purity of more than 99%. The non-adsorbed fraction of chlorotoluene isomers is composed to more than 90% by weight of o-chlorotoluene, the rest being m- and p-chlorotoluene. This mixture is passed, to the isomerization catalyst. The isomerization produces a mixture of about 48% by weight of o-chlorotoluene, 34% by weight of m-chlorotoluene and 18% by weight of p-chlorotoluene. This mixture of isomers is again treated, ie. p-chlorotoluene is isolated. The non-adsorbed chlorotoluenes are again passed to the isomerization catalyst.

When operating in the generally preferable continuous manner, p-chlorotoluene is isolated from the purified toluene chlorination product and the non-adsorbed mixture of isomers is isomerized and then again passed to isolating step, together with fresh purified toluene chlorination product.

To prepare p- and m-chlorotoluene in a continuous or discontinuous manner, toluene is preferably chlorinated at 15°–75° C. in the presence of titanium tetrachloride. The "purified toluene chlorination product" (ie. after neutralization and separation from toluene and polychlorinated by-products) is three-quarters composed of o-chlorotoluene, the rest being mainly p-isomer in addition to a small amount of m-isomer.

This mixture is first treated with an isomerization catalyst. This produces a mixture of isomers comprising about 47% by weight of o-, 35% by weight of m- and 18% by weight of p-chlorotoluene. p-Chlorotoluene is as completely as possible separated from this mixture and isolated more than 99 percent pure. The non-adsorbed fraction of chlorotoluenes is composed of about 58% by weight of o- and about 42% by weight of m-chlorotoluene. This binary mixture is separated by distillation or adsorption into o- and m-chlorotoluene. This produces more than 99 percent pure m-chlorotoluene. o-Chlorotoluene—in the preferable continuous process together with fresh purified toluene chlorination product—is then passed, to the isomerization catalyst. p-Chlorotoluene is again isolated from the mixture obtained after the isomerization, and the remaining o- and m-isomers are again separated by distillation or adsorption. The remaining o-chlorotoluene is then again returned to the isomerization step.

For the sole isolation of m-chlorotoluene the procedure is as just described above, with the single difference that p-chlorotoluene is not removed but returned to the isomerization catalyst.

It may be mentioned as a particular advantage of the process according to the invention that it has become possible, for the first time, to convert toluene virtually completely into pure p- and/or m-chlorotoluene. Hitherto, in the production of p-chlorotoluene, it had to be accepted that o-chorotoluene, for which there is only a comparatively low commercial demand, would necessarily be obtained.

Hitherto customary processes produce pure m-chlorotoluene not by the direct chlorination of toluene but only in an extremely involved manner by using a round-about approach, for example by diazotization of m-toluidine and subsequent Sandmayer reaction with cuprous chloride.

It may finally be emphasized as a further advantage of the process according to the invention that, unlike in the case of customary processes for preparing p-chlorotoluene, a comparatively high content of m-chlorotoluene in the crude chlorination product is not troublesome. It is thus possible to dispense with the measures hitherto necessary for suppressing the formation of m-chlorotoluene, such as the use of expensive catalyst systems and chlorinating at low temperatures—with which necessarily a low conversion of toluene is associated—affording a not inconsiderable economic benefit. The oxychlorination of toluene by means of HCl and oxygen-containing gases, described in Japanese Patent Application No. 3,009,723, can thus also have been integrated in the process according to the invention.

The example which follows is intended to illustrate the invention in more detail.

EXAMPLE

Determination of the separation factors of various ion-exchanged zeolites for mixtures of p- and o- or p- and m-chlorotoluene For the adsorption experiments, the zeolites, to which 20% of $Al_2O_3$ had been added as a binder, were produced in an extruded form, dried for 12 hours at 120° C. and calcined for 4 hours at temperatures of 400°–500° C. The consolidated profiles were then comminuted, and a grain fraction of 0.8–1.9 mm diameter was screened out for the adsorption experiments. Before the adsorption experiments, the zeolites were activated for 3 hours at 450° C. with nitrogen. The analytically pure chlorotoluenes used were dried with a molecular sieve before their use. The adsorber which was used for the experiments and comprised a 1,000 mm long V4A stainless steel tube of 16 mm internal diameter was electrically heated from the outside. The mixtures of isomers were fed at an LHSV of 0.5 by means of a metering pump via an evaporator to the adsorber. (LHSV=liquid hourly space velocity).

The adsorption capacity and selectivity of the zeolites were determined using an equimolar mixture of o- and p-chlorotoluene at 170° C. and under atmospheric pressure. After saturation of the zeolites with p-chlorotoluene and breakthrough of o-chlorotoluene, metering was interrupted, and the adsorber was flushed for 10 minutes with inert gas and then desorbed at 180° C. using benzene or steam. The composition of adsorbate and desorbate were determined by gas chromatography.

To determine the separating power of individual ion-exchanged zeolites, and for exactly comparing them with one another, their $\alpha_{para/ortho}$ separation factors for the equimolar mixture of p- and o-chlorotoluene were determined using the following equation:

$$\alpha_{para/ortho} = \frac{[para]/[ortho] \text{ in the adsorbed phase}}{[para]/[ortho] \text{ in the non-adsorbed phase}}$$

The results of the separation factors, determined under dynamic conditions, for the modified zeolites investigated are summarized in the following table:

| Zeolite | Degree of exchange | $\alpha_{para/ortho}$ separation factor |
|---|---|---|
| NaX | $Na^+$ (100%) | 0.73 |
| KNaX | $K^+$ (70%) | 0.98 |
| NaY | $Na^+$ (100%) | 0.63 |
| KNaY | $K^+$ (25%) | 0.83 |
| KNaY | $K^+$ (72%) | 1.55 |
| KNaY | $K^+$ (94%) | 2.30 |
| BaNaY | $Ba^{2+}$ (76%) | 1.83 |
| KBaNaY | $K^+, Ba^{2+}$ (47%, 30%) | 2.35 |
| $KNH_4NaY$ | $K^+, NH_4^+$ (77%, 17%) | 3.05 |
| K-ZSM-5 | $K^+$ (70%) | 2.85 |

The corresponding separation factors for equimolar mixtures of p- and m-chlorotoluene were determined analogously. These measurements did not produce any serious deviations of the p-chlorotoluene selectivity compared with mixtures of p- and o-chlorotoluene. The values obtained are shown in the following table:

| Zeolite | Degree of exchange | $\alpha_{para/meta}$ separation factor |
|---|---|---|
| KNaY | $K^+$ (25%) | 0.90 |
| KNaY | $K^+$ (94%) | 2.27 |
| KBaNaY | $K^+, Ba^{2+}$ (47%, 30%) | 2.29 |
| $KNH_4NaY$ | $K^+, NH_4^+$ (50%, 43%) | 2.47 |
| $KNH_4NaY$ | $K^+, NH_4^+$ (77%, 17%) | 3.15 |
| K-ZSM-5 | $K^+$ (70%) | 3.35 |

Adsorptive separation of p-chlorotoluene from o- and m-chlorotoluene

A mixture of isomers, comprising 52.6% by weight of o-chlorotoluene, 34.5% by weight of m-chlorotoluene and 12.9% by weight of p-chlorotoluene, was passed over a K-ZSM-5 zeolite modified by 30 minutes' precoking with toluene at 600° C. A distribution of isomers of 59.9% by weight of o-chlorotoluene, 39.3% by weight of m-chlorotoluene and 0.79% by weight of p-chlorotoluene was obtained at the outlet of the above-mentioned adsorber, under steady state conditions, at a WHSV of 0.2 h$^{-1}$, and a temperature of 180° C. and under atmospheric pressure.

Continuous separation of p-chlorotoluene

A reaction mixture obtained by chlorination of toluene at 50° C. in the presence of FeCl$_3$ was freed by distillation from unconverted toluene and polychlorinated by-products. The "purified toluene chlorination product" thus obtained comprised 64% by weight of o-chlorotoluene, 2.6% by weight of m-chlorotoluene and 33.3% by weight of p-chlorotoluene. This mixture was passed through a fixed bed adsorber containing a Y zeolite modified by means of potassium. This selectively adsorbed p-chlorotoluene at 200° C. and under 5 bar.

The mixture leaving the adsorber was passed at 220° C. and under 30 bar through a tube reactor containing a dealuminated H mordenite as isomerization catalyst. This isomerized the mixture. The mixture leaving the reactor was returned to the adsorber for renewed adsorption of p-chlorotoluene. The mixture was passed through the adsorber together with fresh purified toluene chlorination product.

The mixture entering the adsorber contained, in steady state operation, 51.8% by weight of o-chlorotoluene, 29.1% by weight of m-chlorotoluene and 19.2% by weight of p-chlorotoluene. Adsorption took place at a WHSV of 0.3 h$^{-1}$. The mixture leaving the adsorber contained 63.2% by weight of o-chlorotoluene, 35.6% by weight of m-chlorotoluene and 1.2% by weight of p-chlorotoluene. This mixture was converted at a WHSV of 2 h$^{-1}$, in the isomerization reactor, into a mixture composed of 48.9% by weight of o-chlorotoluene, 35% by weight of m-chlorotoluene and 16.1% by weight of p-chlorotoluene and returned, as stated, to the adsorber.

We claim:

1. A continuous process for preparing m-chlorotoluene which comprises the steps of:
   (a) chlorinating toluene to form a toluene chlorination product rich in o-chlorotoluene;
   (b) neutralizing the chlorination product and separating-off by distillation unreacted toluene and higher chlorinated by-products to obtain a purified toluene chlorination product rich in o-chlorotoluene;
   (c) treating the purified toluene chlorination product with an isomerization catalyst comprising a zeolite of the pentasil type to form an isomerization product with increased content of m-chlorotoluene;
   (d) isolating p-chlorotoluene from the isomerization product by selective adsorption of p-chlorotoluene onto a mesoporous or macroporous Y zeolite K$^+$ or Ba$^{2+}$ exchanged and subsequent desorption of p-chlorotoluene to obtain desorbed p-chlorotoluene and an unadsorbed phase lean in p-chlorotoluene and rich in o- and m-chlorotoluene;
   (e) recycling the desorbed p-chlorotoluene to step (c);
   (f) separating the unadsorbed phase by distillation or adsorption into o- and m-chlorotoluene;
   (g) removing the separated m-chlorotoluene; and
   (h) recycling the o-chlorotoluene to step (c).

2. A continuous process for preparing p-chlorotoluene which comprises the steps of:
   (a) chlorinating toluene to form a toluene chlorination product rich in o-chlorotoluene;
   (b) neutralizating the chlorination product and separating-off by distillation unreacted toluene and higher chlorinated by-products to obtain a purified toluene chlorination product rich in o-chlorotoluene;
   (c) isolating p-chlorotoluene from the purified toluene chlorination product, by selective adsorption of p-chlorotoluene onto a mesoporous or macroporous Y zeolite K$^+$ or Ba$^{2+}$ exchanged and subsequent desorption of p-chlorotoluene to obtain an unadsorbed phase lean in p-chlorotoluene and rich in o-chlorotoluene;
   (d) removing the desorbed p-chlorotoluene;
   (e) treating the unadsorbed phase with an isomerization catalyst comprising a zeolite of the pentasil type to form an isomerization mixture with increased content of m- and p-chlorotoluene; and
   (f) recycling said isomerization mixture to step (c).

3. A continuous process for preparing p-chlorotoluene and m-chlorotoluene which comprises the steps of:
   (a) chlorinating toluene to form a toluene chlorination product;
   (b) neutralizing the chlorination product and separating-off by distillation unreacted toluene and higher chlorinated by-products to obtain a purified toluene chlorination product rich in o-chlorotoluene;
   (c) treating the purified toluene chlorination product with an isomerization catalyst comprising a zeolite of the pentasil type to form an isomerization product with increased content of m- and p-chlorotoluene;
   (d) isolating p-chlorotoluene from the isomerization product by selective adsorption of p-chlorotoluene onto a mesoporous or macroporous Y zeolite K$^+$ or Ba$^{2+}$ exchanged and subsequent desorption of p-chlorotoluene to obtain desorbed p-chlorotoluene and an unadsorbed phase lean in p-chlorotoluene and rich in o- and m-chlorotoluene;
   (e) removing the desorbed p-chlorotoluene;
   (f) separating the unadsorbed phase by distillation or adsorption into o- and m-chlorotoluene;
   (g) removing the separated m-chlorotoluene; and
   (h) recycling the o-chlorotoluene to step (c).

* * * * *